US006465465B1

(12) United States Patent
Marx et al.

(10) Patent No.: US 6,465,465 B1
(45) Date of Patent: Oct. 15, 2002

(54) PROCESS FOR THE TREATMENT OF ERECTILE DYSFUNCTION AND PRODUCT THEREFOR

(75) Inventors: Degenhard Marx, Radebeul; Norbert Höfgen, Medingen; Ute Egerland, Radebeul; Stefan Szelényi, Schwaig; Thomas Kronbach, Radebeul, all of (DE)

(73) Assignee: Arzneimittelwerk Dresden GmbH, Radebeul (DE)

( * ) Notice: Subject to any disclaimer, the term of this patent is extended or adjusted under 35 U.S.C. 154(b) by 0 days.

(21) Appl. No.: 09/779,925

(22) Filed: Feb. 8, 2001

Related U.S. Application Data
(60) Provisional application No. 60/189,219, filed on Mar. 14, 2000.

(51) Int. Cl.[7] .................. A61K 31/50; C07D 471/04
(52) U.S. Cl. ........................ 514/250; 544/346
(58) Field of Search ............... 544/346; 514/250

(56) References Cited

U.S. PATENT DOCUMENTS

| | | | | |
|---|---|---|---|---|
| 5,055,465 A | * | 10/1991 | Davey ............ | 514/228.2 |
| 5,166,344 A | * | 11/1992 | Davey ............ | 544/58.6 |
| 5,723,463 A | * | 3/1998 | Hofgen et al. ........ | 514/250 |

FOREIGN PATENT DOCUMENTS

| | | |
|---|---|---|
| DE | 4228095 | 3/1994 |
| DE | 19510965 | 9/1996 |
| DE | 19728301 | 7/1999 |
| EP | 400583 | 12/1990 |
| EP | 736532 | 10/1996 |
| WO | PCT/JP93/00357 | 3/1993 |

OTHER PUBLICATIONS

Terrett et al., Sildenafil (Viagra) a potent and selective, etc., Bioorganic and Medic. Chemistry Ltr. 6, 15, 1819–1824, 1996.

Truss et al., Phosphodiesterase Inhibitors, etc., Drugs of Today, 34, 805–812, 1998.

Polymeropoulos et al., Peptide binding site model for :PDE 4 inhibitors, 18 Quant. Struct. –Act. Relat. (1999) 543–547.

Dent et al., Effects of a selective PDE4 inhibitor D–22888 on human airways, etc., 11 Pulm. Pharmacol. Ther. (1998).

Davey et al., Novel compounds possessing potent cAMP and cGMP phosphodiesterase inhibitory activity, etc., 34 J. Med. Chem., 1991, 2671–2677.

* cited by examiner

Primary Examiner—Johann Richter
Assistant Examiner—Ebenezer Sackey
(74) Attorney, Agent, or Firm—Fulbright & Jaworski L.L.P.

(57) ABSTRACT

The invention relates to the use of pyrido[3,2-e]-pyrazinones of formula 1 as inhibitors of phosphodiesterase 5 for the treatment of erectile dysfunction (impotence).

8 Claims, No Drawings

US 6,465,465 B1

PROCESS FOR THE TREATMENT OF ERECTILE DYSFUNCTION AND PRODUCT THEREFOR

This is a nonprovisional application based on provisional application No. 60/189,219, filed on Mar. 14, 2000, now lapsed.

FIELD OF INVENTION

This invention relates to a therapeutic process for the use of pyrido[3,2-e]-pyrazinones of Formula 1 as active ingredients for the treatment of erectile dysfunction (impotence), new pyrido[3,2-e]pyrazinones, as well as to pharmaceutical compositions containing these compounds.

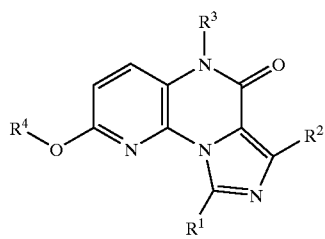

BACKGROUND

Impotence in a man can be defined as the inability to engage in sexual intercourse because of the absence of an erection and/or because of the failure to ejaculate. One speaks of erectile dysfunction, if the erection, with respect to strength or duration, is insufficient for sexual intercourse.

Erectile disorders affect about 10% of the male population. About 52% of men between the ages of 40 and 70 are affected. Several million men worldwide suffer from this disease (about 7.5 million in Germany alone), which in most cases is due to organic causes and less frequently due to mental causes. Erectile dysfunction is a widespread problem among older men, particularly if other chronic diseases are present, such as a high blood pressure, arteriosclerosis and diabetes.

Although different active ingredients can induce an erection, these act only after an injection directly into the penis (intracavernous, i.c.) or instillation into the urethra (intraurethral). This form of pharmacological therapy has been available for more than 10 years and involves the i.c. injection of vasoactive substances, such as papaverin, phenoxybenzamine, phenotolamine, moxisylyte and prostaglandin El (PGEI). However, the i.c. use of these substances frequently is accompanied by serious side effects such as priapismus, pain or penile fibrosis. PGE, can be used intraurethrally and nitroglycerin and minoxidil transdermally (on the penis). However, this can cause side effect in the man as well as in the partner.

Surgical intervention by implanting a prosthesis is an alternative to pharmacological therapy. However, because of the anticipated late complications (infections, blood circulation disorders), this form of therapy is hardly accepted by patients.

The introduction of sildenafil (Viagra®) by Pfizer in the USA and in Europe was a breakthrough in the treatment of erectile dysfunction. Sildenafil is an orally effective phosphodiesterase 5-inhibitor (PDE5 inhibitor), which does not cause an erection directly, but intensifies the action of nitric oxide (NO), which is released in the penis by sexual stimulation. NO, like its second messenger cGMP, brings about a vascular expansion in the corpus cavernosum (cavernous body), so that more blood, which brings about the erection, can flow in.

Phosphodiesterases (PDE) are an isoenzyme family, to which 10 different isoenzymes can so far be assigned. By hydrolysis, PDE enzymes split cyclic guanosine-3',5'-monophosphate (cGMP) or cyclic adenosine-3',5'-monophosphate (cAMP), which occur as 'second messengers' in a plurality of cells. The phosphodiesterase 5 (PDE 5) is cGMP-specific and dominates in the tissue of human corpus cavernosum.

The inhibition of the PDE 5 in human corpus cavernosum leads to an increase in the intracellular cGMP level, induced by NO. A relaxation of the smooth musculature of the corpus cavernosum and, consequently, an erection is associated with this.

Inhibitors of PDE 5 accordingly are therapeutic agents, which are suitable in the case of indication of erectile dysfunction.

European patent 0 400 583 relates to imidazoquinoxalines of the formula

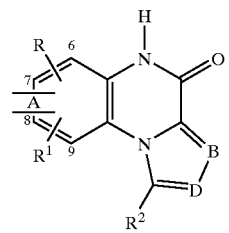

wherein A is nitrogen or CH in positions 7 or 8, B and D are nitrogen or CH or a substituted carbon atom and R, $R^1$, $R^2$ are hydrogen or different organic substituents. These compounds are said to have a vasodilating effect.

In addition to various imidazo[1,2-a]-quinoxalinones, D. D. Davey et al. (J. Med. Chem. 34 (1991), 2671–2677) also described two imidazo[1,5-a]-pyrido[3,2-e]pyraxinones of formula

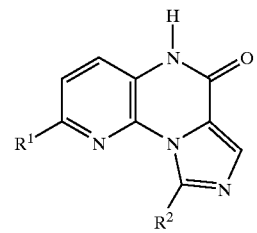

in which, on the one hand $R^1$ is H, and $R^2$ is $C_2H_5$, and, on the other, $R^1$ is 2-methylimidazolo-, and $R^2$ is $CH_3$. Both compounds are PDE 3 inhibitors with a positive inotropic effect.

Patent application No. WO 93/20 077 relates to imidazoquinoxalinones of the formula

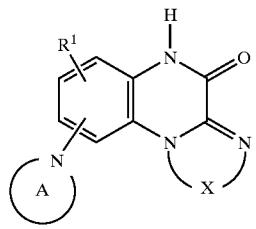

wherein A is a 5-membered heterocyclic ring with 2 or 3 nitrogen atoms in the ring, $R^1$ is $NO_2$ or $CF_3$, and X is a variety of chains, with up to 4 chain elements, some of which contain nitrogen. These compounds are described as glutamate receptor antagonists with psychotropic and anti-ischemic activity.

In German patent application No. 199 02 082, imidazo [1,5-a]-pyrido[3,2-e]-pyrazinones of the formula

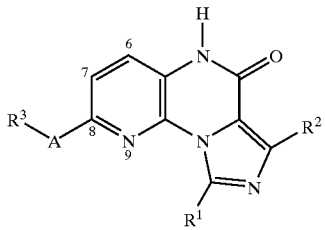

are described, which are inhibitors of PDE 5. For these compounds, which in each case are unsubstituted in the 5 position, the use for the treatment of erectile dysfunction is claimed. According to German patent application No. 199 61 302 some of these compounds are dual inhibitors of PDE 3 and PDE 5. For these compounds, the use for different heart and circulatory diseases is also claimed.

In German patent No. 195 10 965, describes pyrido[3,2-e]-pyrazonones of the formula

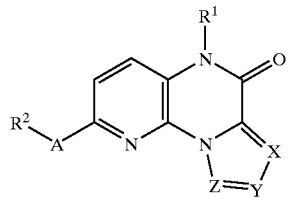

These also include imidazo[1,5-a]-pyrido[3,2-e]-pyrazinones. Antiasthmatic and antiallergic properties were described for the described group of materials.

DESCRIPTION OF THE INVENTION

The present invention relates to a therapeutic process for the treatment of erectile dysfinction, which comprises administering to a patient in need therefor, a pyrido[3,2-e]-pyrazinone of Formula (1)

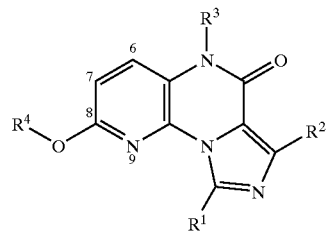

wherein $R^1$, $R^2$, $R^4$ can be the same or different, being a branched or linear $C_{1-4}$ alkyl residue $R^3$ is —$CH_2$—A wherein A is a cyclohexyl residue; or a $C_{6-10}$ monocyclic or bicyclic hydrocarbon which can be substituted once or more times by —F, —Cl, —Br, —$NO_2$, —OH, —$OCH_3$, —$CH_3$ or —CN; or a monocyclic or bicyclic $C_{3-10}$ heteroaromatic hydrocarbon containing 1–4 heteroatoms such as N, S or O, and can be substituted once or more times by —F, —Cl, —Br, —$NO_2$, —OH, —$OCH_3$, —$CH_3$ or CN;

and pharmaceutically acceptable salts thereof.

Typical compounds known for other uses of the foregoing formula include:

5-benzyl-1-ethyl-8-methoxy-3-methyl-imidazo[1,5-a]-pyrido[3,2-e]pyrazinone;

5-benzyl-8-ethoxy-1-ethyl-3-methyl-imidazo[1,5-a]-pyrido[3,2-e]pyrazinone;

5-benzyl-8-ethoxy-1,3-diethyl-imidazo[1,5-a]-pyrido[3,2-e]pyrazinone;

1-ethyl-5-(2-fluorobenzyl)-8-methoxy-3-methyl-imidazo[1,5-a]-pyrido[3,2-e]pyrazinone;

5-(2-chlorobenzyl)-1-ethyl-8-methoxy-3-methyl-imidazo[1,5-a]-pyrido[3,2-e]pyrazinone;

1-ethyl-8-methoxy-5-(4-methoxybenzyl)-8-methoxy-3-methyl-imidazo[1,5-a]-pyrido[3,2-e]pyrazinone;

1-ethyl-5-(4-fluorobenzyl)-3-methyl-imidazo[1,5-a]-pyrido[3,2-e]pyrazinone;

5-(4-chlorobenzyl)-1-ethyl-8-methoxy-3-methyl-imidazo[1,5-a]-pyrido[3,2-e]pyrazinone;

5-(2,6-dichlrobenzyl)-1-ethyl-8-methoxy-3-methyl-imidazol[1,5-a]-pyrido[3,2-e]pyrazinone;

5-(2-chloro-6-fluorobenzyl)-1-ethyl-8-methoxy-3-methyl-imidazo[1,5-a]-pyrido[3,2-e]pyrazinone;

5-(2,6-difluorobenzyl)-1-ethyl-8-methoxy-3-methyl-imidazo[1,5-a]-pyrido[3,2-e]pyrazinone;

1-ethyl-8-methoxy-3-methyl-5-(2,3,6-trifluorobenzyl)-imidazo[1,5-a]-pyrido[3,2-e]pyrazinone;

5-(2-chloro-6-fluorobenzyl)-8-methoxy-3-methyl-1-propyl-imidazo[1,5-a]-pyrido[3,2-e]pyrazinone;

5-(2,6-difluorobenzyl)-8-methoxy-3-methyl-1-propyl-imidazo[1,5-a]-pyrido[3,2-e]pyrazinone;

8-methoxy-3-methyl-1-propyl-5-(2,3,6-trifluorobenzyl)-imidazo[1,5-a]-pyrido[3,2-e]pyrazinone;

5-[(3,5-dimethylisoxazol-4-yl)-methyl-1-ethyl-8-methoxy-3-methyl-imidazo[1,5-a]-pyrido[3,2-e] pyrazinone;

1-ethyl-8-methoxy-3-methyl-5-(4-pyridylmethyl)-imidazo[1,5-a]-pyrido[3,2-e]pyrazinone;

1-ethyl-8-methoxy-2-methyl-5-(4-pyridylmethyl-imidazo [1,5-a]-pyrido[3,2-e]pyrazinone hydrochloride;

5-[(2,6-dichloropyrid-4-yl)-methyl]-1-ethyl-8-methoxy-3-methyl-imidazo[1,5-a]-pyrido[3,2-e]pyrazinone.

Compounds of Formula (1) in which A is a cyclohexyl residue, are new, such as for example 5-cyclohexyl-1-ethyl-8-methoxy-3-methyl-imidazo[1,5-a]-pyrido[3,2-e] pyrazinone.

It is an important feature of the present invention that the compounds of Formula 1 have a nitrogen atom in position 9 as an essential structural prerequisite for the present inventive use for the treatment of erectile dysfunction.

The pharmaceutically acceptable salts of the compounds of Formula 1, can be suitably obtained by neutralizing the bases with inorganic or organic acids, or by neutralizing the acids with inorganic or organic bases, or by quaternizing tertiary amines to quaternary ammonium salts. Some of the compounds of Formula 1 of the present invention are known from German patent No. 195 10 965, to which reference was already made hereinabove in describing the state of the art. Pyrido[3,2-e]-pyrazinones were referred thereto as dual inhibitors of PDE 4 and PDE 5, as anti-asthmatic or anti-allergic agents.

The compounds of Formula 1 are distinguished in that their inhibitory effect on PDE 5 is particularly pronounced. It is the essence of the present invention that the compounds of Formula 1, due to their principle of action, are particularly suitable for use as therapeutic agents for the treatment of erectile dysfunction.

It is a particular advantage of the compounds of the present invention that they highly selectively affect the cGMP level in human tissue, but not the cAMP level. This was shown for human tissue of the heart as well as of the penis. With this selectivity, the risk of cardiovascular side effects is minimized. In regard to the cGMP selectivity, the compounds of the present invention are superior to the standard therapeutic agent sildenafil.

The compounds of Formula 1 can be administered systemically, for example, intravenously, intramuscularly or subcutaneously, as well as orally, bucally or sublingually. A topical application, for example, by inhalation or intranasally, is also possible. The oral administration of 5 to 200 mg of the compound before sexual intercourse represents a suitable treatment regimen.

Drugs which contain one or more of the compounds of Formula 1 contain in addition to the conventional, physiologically tolerated carriers and/or diluents or inactive ingredients. The present invention also relates to a method for producing these drugs.

The compounds of Formula 1 and the drugs, which contain the compounds of Formula 1, can be used individually or in combination with one another.

As a further feature of the present invention, the compounds of Formula 1 can also be used as veterinary therapeutic agents for the prophylaxis and treatment of erectile dysfunction in male mammals. In determining the dosage, the administration schedule and the pharmaceutical formulation of the compound, species differences and the requirements of veterinary practice are taken into consideration.

The compounds of Formula 1 are strong inhibitors of phosphodiesterase 5. Their therapeutic potential is confirmed in vitro, for example, by the reinforcement of the action of NO on the intracellular cGMP level in fibroblasts of the rat, the selectivity of the effect on the cAMP and cGNW levels in human tissue and by the relaxation of the human corpus cavernosum.

The following compounds represent suitable examples of the compounds of Formula 1 which can be used in accordance with the therapeutic process of the present invention:

| Example | -$R^1$ | -$R^2$ | -$R^3$ | -$R^4$ | Melting point [° C.] |
|---|---|---|---|---|---|
| 1 | —$C_2H_5$ | —$CH_3$ | —$CH_2C_6H_{11}$ | —$CH_3$ | 136–138 (Ethanol) |
| 2 | —$C_2H_5$ | —$CH_3$ | —$CH_2C_6H_5$ | —$CH_3$ | 166–167 (Acetone) |
| 3 | —$C_2H_5$ | —$CH_3$ | —$CH_2C_6H_5$ | —$C_2H_5$ | 162–163 (Acetone) |
| 4 | —$C_2H_5$ | —$C_2H_5$ | —$CH_2C_6H_5$ | —$C_2H_5$ | 159–161 (Acetone) |
| 5 | —$C_2H_5$ | —$CH_3$ | —$CH_2C_6H_4$(2-F) | —$CH_3$ | 186–187 (Ethanol) |
| 6 | —$C_2H_5$ | —$CH_3$ | —$CH_2C_6H_4$(2-Cl) | —$CH_3$ | 245–246 (DMF) |
| 7 | —$C_2H_5$ | —$CH_3$ | —$CH_2C_6H_4$(4-$OCH_3$) | —$CH_3$ | 156–158 (Ethanol) |
| 8 | —$C_2H_5$ | —$CH_3$ | —$CH_2C_6H_4$(4-F) | —$CH_3$ | 189–191 (DMF) |
| 9 | —$C_2H_5$ | —$CH_3$ | —$CH_2C_6H_4$(4-Cl) | —$CH_3$ | 201–202 (DMF) |
| 10 | —$C_2H_5$ | —$CH_3$ | —$CH_2C_6H_4$(2,6-di-Cl) | —$CH_3$ | 209–212 (Toluene) |
| 11 | —$C_2H_5$ | —$CH_3$ | —$CH_2C_6H_4$(2-Cl,6-F) | —$CH_3$ | 197–200 (Acetone) |
| 12 | —$C_2H_5$ | —$CH_3$ | —$CH_2C_6H_4$(2,6-di-F) | —$CH_3$ | 177–180 (Acetone) |
| 13 | —$C_2H_5$ | —$CH_3$ | —$CH_2C_6H_4$(2,3,6-tri-F) | —$CH_3$ | 183–185 (Acetone) |
| 14 | —$C_2H_7$ | —$CH_3$ | —$CH_2C_6H_4$(2-Cl,6-F) | —$CH_3$ | 159–162 (Acetone) |
| 15 | —$C_2H_7$ | —$CH_3$ | —$CH_2C_6H_4$(2,6-di-F) | —$CH_3$ | 171–172 (Acetone) |
| 16 | —$C_2H_7$ | —$CH_3$ | —$CH_2C_6H_4$(2,3,6-tri-F) | —$CH_3$ | 197–199 (Acetone) |
| 17 | —$C_2H_5$ | —$CH_3$ | | —$CH_3$ | 188–190 (Ethanol) |
| 18 | —$C_2H_5$ | —$CH_3$ | | —$CH_3$ | 198–200 (Ethanol) |
| 19 | —$C_2H_5$ | —$CH_3$ | | —$CH_3$ | 237–240 zers. (DMF) |
| 20 | —$C_2H_5$ | —$CH_3$ | | —$CH_3$ | 254–256 (Ethanol) |

PDE 5 activity is determined in enzyme preparations from human thrombocytes. Human blood was anti-coagulated with citrate. By centrifuging at 700 g for 20 minutes at room temperature, the thrombocyte-rich plasma in the supernatant is separated from the erythrocytes and leukocytes. The thrombocytes are lysed by ultrasound and used in the PDE 5 assay. With a few modifications, the phosphodiesterase activity is determined by the method described by Thompson et al. (Thompson, W. J., Appleman, M. M., Assay of cyclic nucleotide phosphodiesterase and resolution of multiple molecular forms of the enzyme, Adv. Cycl. Nucl. Res. 1979, 10, 69–92). The reaction mixtures contain 50 mM of tris HCl (pH 7.4), 5.5 mM of $MgCl_2$, the inhibitors in variable concentrations, the enzyme preparation and the fuirther components necessary for determining the individual isoenzymes PDE 5 (see below). The reaction is started by the addition of the substrate, 0.5 μM of [$^3$H] cGMP (approximately 6,000 CPM/test). The final volume is 100 mV. Test substances are prepared as stock solutions in DMSO. The DMSO concentration in the reaction mixture is 1% v/v. The PDE 5 activity is not affected by this concentration of DMSO. After the reaction is started by the addition of substrate, the samples are incubated for 30 minutes at 37° C. The reaction is stopped by heating the test tubes for 2 minutes at 110° C. The samples remain for a further 10 minutes in ice. The addition of 30 μL of 5'-nucleotidase (1 mg/mL, from a Crotalus adamanteus snake poison suspension) is followed by an incubation for 10 minutes at 37° C. The samples are stopped on ice. After the addition of 400 µL of a (1:1:1) mixture of Dowex, water and ethanol, the samples are mixed well and incubated once again for 15 minutes on ice. The reaction vessels are centrifuged for 20 minutes at 3,000 g. Subsequently, 200 µL aliquots of the supernatant are transferred directly to scintillation vessels. After the addition of 3 mL of scintillator, the samples are measured in the Betacounter. The in each case nonspecific enzyme activities are determined in the presence of 100 µM of IBMX for the determination of the PDE 5 and subtracted from the test values.

For the inventive compounds, $IC_{50}$ values ranging from $10^{-9}$ to $10^{-5M}$ were determined for the inhibition of the phosphodiesterase 5. For example, the following values were determined for selected values:

| Example | $IC_{50}$ (µmoles/l) |
|---------|----------------------|
| 1       | 0.025                |
| 2       | 0.203                |
| 5       | 0.059                |
| 7       | 0.104                |
| 8       | 0.126                |
| 9       | 0.112                |
| 10      | 0.132                |
| 11      | 0.019                |
| 12      | 0.038                |
| 13      | 0.016                |
| 14      | 0.008                |
| 15      | 0.002                |
| 16      | 0.005                |

Induction of NO Production in Fibroblasts (rat)

Rat fetal lung fibroblast cells (RFL-6) represent a suitable medium for investigating influence of the action of NO on the intracellular cGNP level (Ishii et al. 1991). The basic mechanism can be transferred to the smooth vascular musculature of the corpus cavemosum.

As a fuinction of the concentration, the inventive compounds reinforce the increase in the intracellular cGXD level induced by the NO donor S-nitroso-N-acetyl-D,L-penicillamine.

For example, compound 13, at a concentration of 0.10 µmoles/l significantly induces an increase in the cGNW level. The effectiveness of compound 13 in this connection is 1000 times that achieved by the use of the nonspecific PDE inhibitor 3-isobutyl-1-ethylxanthine (IBMX).

Influencing the cCAMP and cGMP Levels in Human Tissue

The selectivity of the effect on the cGNW level in comparison to the cCAMP level by the PDE 5 inhibitors gives indications or possible side effects of the substances, above all with respect to the cardiovascular system.

Strips of human atrium and human corpus cavernosum are incubated for 10 minutes with the test compounds at a concentration of 1.0 µmoles/L The preparations are frozen with liquid nitrogen and the resulting levels of the cyclic nucleotides are determined.

In both tissues, the inventive compounds selectively affect the cGMP level. In human atrium tissue for example, the cGMP level is increased by 247% by compound 11 and, on the other hand, the cCAMP level only by 11%. In human corpus cavemosum tissue, the cGMP level, on the other hand, is increased by 214% by compound 11 and the cCAMP level only by 80%.

With respect to this selectivity, the inventive compounds are superior to the standard therapeutic agent, sildenafil. In human atrium tissue, the cGMP level is increased by 147% by sildenafil and the cCAMP level at the same time by 240%. In human corpus cavemosum tissue, the cGMP level is increased only by 15% by sildenafil and the cCAMP level, on the other hand, by 238%.

In vitro Relaxation of Human Corpus Cavemosum

Strips of human corpus cavernosum are pre-contracted in an organ bath with noradrenalin. For test compounds, the relaxation is determined as a function of the concentration.

The inventive compounds have a relaxing effect, as a function of the concentration, on the corpus cavernosum strips pre-contracted with noradrenalin. For example, an $EC_{50}$ value of 0.15 µmoles/l was determined for compound 13.

We claim:

1. A process for the treatment of erectile dysfinction, which comprises administering to a patient in need therefor a pyrido[2,3-e]pyrazinone of Formula (1)

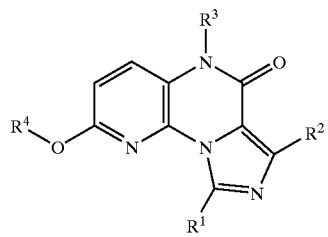

wherein
$R^1$, $R^2$, and $R^4$ can be the same or different, and being a linear or branched $C_{1-4}$ alkyl radical, and
$R^3$ is —$CH_2$—A wherein
A is a cyclohexyl radical; or a $C_{6-10}$ monocyclic or bicyclic hydrocarbon which can be substituted once or more times by —F, —Cl, —Br, —$NO_2$, —OH, —$OCH_3$, —$CH_3$, or —CN; or a monocyclic or bicyclic $C_{3-10}$ heteroaromatic hydrocarbon containing 1–4 heteroatoms, and can be substituted one or more times by —F, —Cl, —Br, —OH, —$OCH_3$, —$CH_3$, or —CN, and pharmaceutically acceptable salt thereof.

2. The process of claim 1, wherein said heteroatom is N, S, or O.

3. The process of claim 1, wherein said pyrido[2,3-e] pyrazinone is a pharmaceutically acceptable salt of a compound of Formula (1), obtained by neutralization of a base with an organic or inorganic acid, or by neutralization of an acid with an organic or inorganic base, or by quaternization of a tertiary amine to a quaternary ammonium salt.

4. The process of claim 1, wherein said pyrido[2,3-e] pyrazinone of Formula (1) is
   5-cyclohexyl-1-ethyl-8-methoxy-3-methyl-imidazo[1,5-a]-pyrido[3,2-e]pyrazinone;
   5-benzyl-1-ethyl-8-methoxy-3-methyl-imidazo[1,5-a]-pyrido[3,2-e]pyrazinone;
   5-benzyl-8-ethoxy-1-ethyl-3-methyl-imidazo[1,5-a]-pyrido[3,2-e]pyrazinone;
   5-benzyl-8-ethoxy-1,3-diethyl-imidazo[1,5-a]-pyrido[3,2-e]pyrazinone;

1-ethyl-5-(2-fluorobenzyl)-8-methoxy-3-methyl-imidazo[1,5-a]-pyrido[3,2-e]pyrazinone;

5-(2-chlorobenzyl)-1-ethyl-8-methoxy-3-methyl-imidazo[1,5-a]-pyrido[3,2-e]pyrazinone;

1-ethyl-8-methoxy-5-(4-methoxybenzyl)-8-methoxy-3-methyl-imidazo[1,5-a]-pyrido[3,2-e]pyrazinone;

1-ethyl-5-(4-fluorobenzyl)-3-methyl-imidazo[1,5-a]-pyrido[3,2-e]pyrazinone;

5-(4-chlorobenzyl)-1-ethyl-8-methoxy-3-methyl-imidazo[1,5-a]-pyrido[3,2-e]pyrazinone;

5-(2,6-dichlrobenzyl)-1-ethyl-8-methoxy-3-methyl-imidazo[1,5-a]-pyrido[3,2-e]pyrazinone;

5-(2-chloro-6-fluorobenzyl)-1-ethyl-8-methoxy-3-methyl-imidazo[1,5-a]-pyrido[3,2-e]pyrazinone;

5-(2,6-difluorobenzyl)-1-ethyl-8-methoxy-3-methyl-imidazo[1,5-a]-pyrido[3,2-e]pyrazinone;

1-ethyl-8-methoxy-3-methyl-5-(2,3,6-trifluorobenzyl)-imidazo[1,5-a]-pyiido[3,2-e]pyrazinone;

5-(2-chloro-6-fluorobenzyl)-8-methoxy-3-methyl-1-propyl-imidazo[1,5-a]-pyrido[3,2-e]pyrazinone;

5-(2,6-difluorobenzyl)-8-methoxy-3-methyl-1-propyl-imidazo[1,5-a]-pyrido[3,2-e]pyrazinone;

8-methoxy-3-methyl-1-propyl-5-(2,3,6-trifluorobenzyl)-imidazo[1,5-a]-pyrido[3,2-e]pyrazinone;

5-[(3,5-dimethylisoxazol-4-yl)-methyl-1-ethyl-8-methoxy-3-methyl-imidazo[1,5-a]-pyrido[3,2-e]pyrazinone;

1-ethyl-8-methoxy-3-methyl-5-(4-pyridylmethyl)-imidazo[1,5-a]-pyrido[3,2-e]pyrazinone;

1-ethyl-8-methoxy-2-methyl-5-(4-pyridylmethyl-imidazo[1,5-a]-pyrido[3,2-e]pyrazinone hydrochloride;

5-[(2,6-dichloropyrid-4-yl)-methyl]-1-ethyl-8-methoxy-3-methyl-imidazo[1,5-a]-pyrido[3,2-e]pyrazinone.

5. The pyrido[2,3-e] pyrazinone compound which is 5-cyclohexyl-1-ethyl-8-methoxy 3-methyl-imidazo[1,5-a]-pyrido[3,2-e]pyrazinone.

6. A pyrido[2,3-e]pyrazinone of Formula (1)

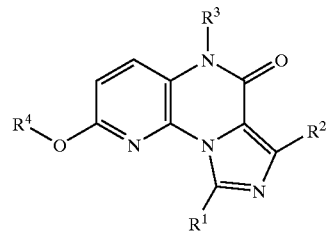

wherein $R^1$, $R^2$, and $R^4$ can be the same or different, and being a linear or branched $C_{1-4}$ alkyl radical, and $R^3$ is —$CH_2$—A wherein
  A is a cyclohexyl radical optionally substituted one or more times by —F, —Cl, —Br, —OH, —$OCH_3$, —$CH_3$, or —CN.

7. A pharmaceutically acceptable salt of the pyrido[2,3-e]pyrazinone of claim 6.

8. A process for selectively influencing the cGMP-level in erectile dysfunction, which comprises, administering to a patient in need therefor a pyrido[2,3-e]pyrazinone of claim 1, or a pharmaceutically acceptable salt thereof.

* * * * *